US007763774B2

(12) United States Patent
Hehl et al.

(10) Patent No.: US 7,763,774 B2
(45) Date of Patent: Jul. 27, 2010

(54) ROOT-SPECIFIC AND XYLEM PARENCHYMA-SPECIFIC PROMOTER

(75) Inventors: Reinhard Hehl, Braunschweig (DE); Heiko Oltmanns, Neukamperfehn (DE); Dietmar Juergen Stahl, Einbeck (DE)

(73) Assignees: KWS SAAT AG, Einbeck (DE); Suedzucker AG, Mannheim (DE)

( * ) Notice: Subject to any disclaimer, the term of this patent is extended or adjusted under 35 U.S.C. 154(b) by 0 days.

(21) Appl. No.: 11/574,719

(22) PCT Filed: Sep. 2, 2005

(86) PCT No.: PCT/DE2005/001540

§ 371 (c)(1),
(2), (4) Date: Jul. 23, 2007

(87) PCT Pub. No.: WO2006/024291

PCT Pub. Date: Mar. 9, 2006

(65) Prior Publication Data

US 2007/0266457 A1    Nov. 15, 2007

(30) Foreign Application Priority Data

Sep. 3, 2004  (DE) ...................... 10 2004 043 207

(51) Int. Cl.
C12N 15/09    (2006.01)
C12N 15/82    (2006.01)
A01H 5/00     (2006.01)
A01H 5/10     (2006.01)

(52) U.S. Cl. ................... 800/287; 800/298; 435/320.1; 536/24.1

(58) Field of Classification Search ........................ None
See application file for complete search history.

(56) References Cited

U.S. PATENT DOCUMENTS 5,459,252 A  * 10/1995  Conkling et al. ............ 800/302
5,929,304 A  *  7/1999  Radin et al. ................. 800/288
2002/0042934 A1 * 4/2002  Staub et al. ................. 800/300

FOREIGN PATENT DOCUMENTS

EP          1 207 204          11/2000
WO    WO 2005040377 A2  *  6/2005

OTHER PUBLICATIONS

Samach et al. (1995) Expression of an amino acid biosynthesis gene in tomato flowers: developmental upregulation and MeJa response are parenchyma-specific and mutually compatible. The Plant journal : for cell and molecular biology, vol. 8, No. 3, pp. 391-406.*
Takahashi et al (2000) The roles of three functional sulphate transporters involved in uptake and translocation of sulphate in Arabidopsis thaliana The Plant Journal 2000 23:2 171.*
Kim et al., (1994) A 20 nucleotide upstream element is essential for the nopaline synthase (nos) promoter activity. Plant Molecular Biology 24: 105-117.*
Mermod, et al., 3.6% identical (Identity_Nuc Database Accession No. ADZ70902, published May 6, 2005, WO2005040377-A2).*
Fickett and Hatzigeorgiou, ((1997) Eukaryotic Promoter Recognition Genome Research 7:861-878.*
Oltmanns et al. Planta (2006) vol. 224, pp. 485-495.*
Kataoka T. et al., Plant Physiology, Dec. 2004; vol. 136, pp. 4198-4204.*
Hiroshi, et al.; *Arabidopsis* AtMYC2 and AtMYB2 Function as Transcriptional Activators in Abscisic Acid Signaling; The Plant Cell, vol. 15, Jan. 2003.
Altschul, et al.; Basic Local Alignment Search Tool; J.Mol. Biol. (1990).
An, Gynheung; Binary Ti Vectors for Plant Transformation and Promoter Analysis; Methods in Enzymology, vol. 153; 1987.
Becker, Detlef, et al.; New plant binary vectors with selectable markers located proximal to the left T-DNA border; Plant Molecular Biology 20, 1992.
Elmayan, Taline, et al.; Evaluation in tobacco of the organ specificity and strength of the rolD promoter, domain A of the 35S promoter and the 35S2 promoter; Transgenic Research 4, 1995 p. 388-396.
Guilfoyle, T. et al.; How Does Auxin Turn On Genes?; Plant Physiol. (1998).
Gaymard, F., et al.; Identification and Disruption of a Plant Shaker-like Outward Channel Involved in K+ Release into the Xylem Sap; Cell, vol. 94, 1998.
Heil, M. et al.; Fitness costs of induced resistance: emerging experimental support for a slippery concept; Trends in Plant Science vol. 7 No. 2; Feb. 2002.
Lindsey, K., et al.; Regeneration and transformation of sugarbeet by Agrobacterium tumefaciens; Plant Tissue Culture Manual B7: 1-13, 1991.
Logemann, E. et al.; Modes of expression and common structural features of the complete phenylalanine ammonia-lyase gene family in parsley; Proc.Natl.Acad.Sci. vol. 92 1995.
Mes, J. et al.; Expression of the Fusarium resistance gene 1-2 colocalizes with the site of fungal containment; The Plant Journal (2000).
Okumoto S. et al.; High Affinity Amino Acid Transporters Specifically Expressed in Xylem Parenchyma and Developing Seeds of *Arabidopsis*; Journal of Biological Chemistry 2002.
Rentsch, D. et al.; Salt Stress-Induced Proline Transporters and Salt Stress-Repressed Broad Specificity Amino Acid Permeases Identified by Suppression of a Yeast Amino Acid Permease-Targeting Mutant; The Plant Cell, vol. 8, 1996.

(Continued)

*Primary Examiner*—Russell Kallis
(74) *Attorney, Agent, or Firm*—Patent Central LLC; Stephen A. Pendorf; Katherine E. Dover

(57) ABSTRACT

The invention relates to a promoter that is provided with tissue-specific activity and is more active in xylem parenchyma cells of plant roots than it is in other cells of said plant. The inventive promoter allows transgenic plants to be produced with particular characteristics: (a) improved xylem charging and discharging processes in the root; (b) improved nitrogen supply; (c) reduced accumulation of harmful nitrogen in the root; (d) improved resistance to salt; (e) improved resistance to stress due to dry conditions; (f) improved tolerance to frost; (g) modified Na+/K+ concentration in the root; (h) greater resistance/tolerance to pathogens.

7 Claims, 10 Drawing Sheets

OTHER PUBLICATIONS

Rushton, P. et al.; Synthetic Plant Promoters Containing Defined Regulatory Elements Provide Novel Insights into Pathogen-and Wound-Induced Signaling; The Plant Cell vol. 14, pp. 749-762; Apr. 2002.

Schiweck, H. et al.; Errechnung der Dicksaft-Nichtzuckermasse aus Rubenanalysen; Zuckerind. 119 (1994).

Shi, H. et al.; The Putative Plasma Membrane Na+/H+ Antiporter SOS1 Controls Long-Distance Na+Transport in Plants; The Plant Cell, vol. 14, 2002.

Takahashi, H. et al.; The roles of three functional sulphate transporters involved in uptake and translocation of sulphate in *Arabidopsis thaliana*; The Plant Journal (2000).

Yu, D. et al.; Evidence for an Important Role of WRKY DNA Binding Proteins in the Regulation of NPR1 Gene Expression; The Plant Cell vol. 13, Jul. 2001.

Sakuta, C. et al.; Vascular Tissue-Specific Gene Expression of Xylem Sap Glycine-Rich Proteins in Root and Their Localization in teh Walls of Metaxylem Vessels in Cucumber; Plant Cell Physiol. 41(5), 2000.

Kloos, D. et al.; Isolation and molecular analysis of six taproot expressed genes frmo sugar beet; Journal of Experimental Botany, vol. 53, Jun. 2002.

* cited by examiner

|—— 8 mm ——|

SEQUENCE LISTING

<160> NUMBER OF SEQ ID NOS: 2

<210> SEQ ID NO 1
<211> LENGTH: 2502
<212> TYPE: DNA
<213> ORGANISM: Beta vulgaris
<220> FEATURE:
<221> NAME/KEY: TATA_signal
<222> LOCATION: (2462)..(2467)

<400> SEQUENCE: 1

| | | | | | |
|---|---|---|---|---|---|
| aagcttctcc | tttgagaagg | agaagtcagt | attacccgtt | caaaagggta | ttgactattg | 60 |
| agtcaccgag | gaatgcgact | cttccaagaa | tcatgattca | agaattccat | gtgacaaaag | 120 |
| gtcacgggaa | ctagttaaag | tgcaagttcc | aaatctcgct | tgttttcgt | ccctccgatt | 180 |
| gttaaatcag | tccactcctt | cctcatcttc | catcattgtt | atagtgtttg | tcaaccatca | 240 |
| acaaaagaac | ttcaatacac | ttatttcaca | atacggacct | ctagattgag | cagctttatc | 300 |
| taagtttgag | ttatttatgt | tattgtaatt | gttatgtaac | aacaagtaaa | gctcaagtta | 360 |
| gtttctttgt | ttttatttgg | ttgcattagc | gttaggatgt | actttcattt | ttaattaatg | 420 |
| caaaattctc | cgttataaaa | aaaagggat | ccctctatgc | cttcataaac | tgcctaattt | 480 |
| ctgcaattga | gatcccaaaa | tagaaacaat | gaatttgaaa | cctaccaatt | tgagtgctgt | 540 |
| gcctaagtcc | taagacccaa | gtcatctcta | atgacacacc | caatctcacc | gagtagatag | 600 |
| gtgatcacta | gaaaatagag | ataaatatga | aacaattttc | ttcttttgt | gtaatttcaa | 660 |
| aagaaatatt | tcacttgttt | tagaacggat | atatatat | atatatatat | atatatat | 720 |
| atatatatat | atatatatat | ataaaagctc | attagaaatt | tgataataga | actagtactt | 780 |
| ttttaatgta | tcttgatggg | ataaccttag | cttgcaaaag | cacactgacg | ttggaatgct | 840 |
| gtcgtttgat | gacattggca | acatttcctt | tcaatttttt | cttccattat | ctcattaatc | 900 |
| cactaggata | ctagcctaat | ggcccattaa | tggtcttcat | tggaaaaatg | tattataaaa | 960 |
| tttattcttc | atggaaatat | aagaaaaggc | cttctaatac | tcccactctc | ccagtgttgg | 1020 |
| aaagaaagtt | gggcagataa | agtttggagc | tccaatcctt | caagtcattt | gtgactgaat | 1080 |
| actgtttatg | ttatgttaat | gggttaggct | tgatgatcca | aaaggtaaca | aaggaaagtt | 1140 |
| ctacaatatc | tcgcgaagat | ttagttatag | agcttagtat | aaaactgtat | catattgaga | 1200 |
| atctatttt | catggggata | ccgtatggag | tcttagtggt | catttggttg | catacggaaa | 1260 |
| attacacttc | ttagcaatat | gtaattccca | tgaaatttca | tttcttatga | agagtacata | 1320 |
| actgttttgg | ttatatactt | ttactatttt | atgagaagtg | aaattccaga | aatttgtgtg | 1380 |
| tttttgttaa | ccaaacaatc | cttcatctt | atatttaaca | agaacttaca | tttcctatgt | 1440 |
| tttgtagtat | caactaaacg | attacttatt | cttgagtcaa | tgtttaaatt | taatactagg | 1500 |
| tagtgtgtat | ttatattatt | atatacgagt | aattttctta | tgatggtgca | aataataatc | 1560 |
| ttttaataa | aattgatgag | tacatattga | actatacgtg | ttgatgtgcg | gatacttcta | 1620 |
| aataagtttt | atatacaact | ttcttatgca | tcacttcatt | taataagaac | aacatatgat | 1680 |
| agcctagtgg | tacattgaca | taacatctga | tattagaggt | cccgggatcg | agtcttacct | 1740 |
| tttgtgagaa | ggatcctcaa | tttttccct | tcttgtaact | tgcaagagac | aaatcacttc | 1800 |
| ttttgatgat | agatgatgcg | atattatgag | aaatgtcata | cacaagataa | ataattccat | 1860 |
| ttttactcga | taatatataa | ctcataattg | tttctgataa | ttcttatcaa | taatatactc | 1920 |

-continued

| | |
|---|---|
| cctccgtcct ctattagttt acccgtattc cttttaagag tgtctcttat tagtttaccc | 1980 |
| cttttattt tttgctattt ttggaatggg accacaaact tttcatcaca cataaattca | 2040 |
| atttaatata aaataatagt ttctctttct ttatatgacc cacaatatta tttctcctaa | 2100 |
| aacttgtgcg aaagaaaggg gtaaactaat agaggacgga gggagtacat cattagtaat | 2160 |
| atatgggtac tcatggtatg catagcgcat tttccatgca ataatattgc aatattgatc | 2220 |
| gactgatcaa catgcaaatc aaatcaccaa tcacaactcg gaactaaggt agtatttgac | 2280 |
| cccaatttat actggggaag tttcactttc agaaatacgt aaacacaaaa acaagtgcgt | 2340 |
| gcatgcgcat tggccattgg agtattgaag tatatcttgt agaggataag caatgtcttg | 2400 |
| gtctttccaa tatcaatata tcattactta gtaatgatat ggtctgcctt ttcctatgct | 2460 |
| atataaaccc tcaaatcctc taactctaaa acccaccaaa tc | 2502 |

<210> SEQ ID NO 2
<211> LENGTH: 1151
<212> TYPE: DNA
<213> ORGANISM: Zea mays
<220> FEATURE:
<221> NAME/KEY: promoter
<222> LOCATION: (1)..(1147)
<220> FEATURE:
<221> NAME/KEY: TATA_signal
<222> LOCATION: (16)..(24)
<220> FEATURE:
<221> NAME/KEY: Intron
<222> LOCATION: (129)..(1133)

<400> SEQUENCE: 2

| | |
|---|---|
| cttcctcgcc cgccgtaata aatagacacc ccctccacac cctctttccc caacctcgtg | 60 |
| ttgttcggag cgcacacaca cacaaccaga tctcccccaa atccacccgt cggcacctcc | 120 |
| gcttcaaggt acgccgctcg tcctcccccc ccctctctac cttctctaga tcggcgttcc | 180 |
| ggtccatggt tagggcccgg tagttctact tctgttcatg tttgtgttag atccgtgttt | 240 |
| gtgttagatc cgtgctgcta gcgttcgtac acggatgcga cctgtacgtc agacacgttc | 300 |
| tgattgctaa cttgccagtg tttctctttg gggaatcctg ggatggctct agccgttccg | 360 |
| cagacgggat cgatttcatg attttttttg tttcgttgca tagggtttgg tttgcccttt | 420 |
| tcctttattt caatatatgc cgtgcacttg tttgtcgggt catcttttca tgcttttttt | 480 |
| tgtcttggtt gtgatgatgt ggtctggttg ggcggtcgtt ctagatcgga gtagaattct | 540 |
| gtttcaaact acctggtgga tttattaatt ttggatctgt atgtgtgtgc catacatatt | 600 |
| catagttacg aattgaagat gatggatgga aatatcgatc taggataggt atacatgttg | 660 |
| atgcgggttt tactgatgca tatacagaga tgcttttgtt cgcttggttg tgatgatgtg | 720 |
| gtgtggttgg gcggtcgttc attcgttcta gatcggagta gaatactgtt tcaaactacc | 780 |
| tggtgtattt attaattttg gaactgtatg tgtgtgtcat acatcttcat agttacgagt | 840 |
| ttaagatgga tggaaatatc gatctaggat aggtatacat gttgatgtgg gttttactga | 900 |
| tgcatataca tgatggcata tgcagcatct attcatatgc tctaaccttg agtacctatc | 960 |
| tattataata aacaagtatg ttttataatt attttgatct tgatatactt ggatgatggc | 1020 |
| atatgcagca gctatatgtg gatttttta gccctgcctt catacgctat ttatttgctt | 1080 |
| ggtactgttt cttttgtcga tgctcaccct gttgtttggt gttacttctg caggtcgagt | 1140 |
| ggccaccatg g | 1151 |

ROOT-SPECIFIC AND XYLEM PARENCHYMA-SPECIFIC PROMOTER

The present invention concerns a promoter and the use thereof as well as transgenic plants.

Higher plants contain a vascular system, the xylem, in which the upward transport of water and mineral nutrients takes place.

The charging of the xylem in the root is regulated via the xylem parenchyma, which jackets the xylem strands. The xylem parenchyma cells of the root thus represent an important control point for the material uptake in the xylem. For this purpose the xylem parenchyma cells contain specific proton pumps, water channels and ion channels.

With its physiological importance for metabolism, the xylem parenchyma opens a series of possibilities for undertaking genetic changes in plants. Influence on the nutrient transport can occur for example via certain proteins which are active primarily in xylem parenchyma.

Promotors are already known, which are active inter alia in xylem parenchyma cells. However the activity of these promoters is either not limited exclusively to xylem parenchyma cells, or the promoters are not primarily active in the roots. Thus the activity of the Sultr2.1-promoter is also evidenced in leaf phloem (Takehashi et al., 2000), and the SOS1-promoter is also active in the terminal cells of root tips (Shi et al., 2002). The I2-promoter of the resistance gene I2 of the tomato is active primarily in the xylem parenchyma cells of the sprout and besides this also in the root, the leaf and the tomato fruit (Mes et al., 2000). The high affinity amino acid transporter AAP6 from *A. thaliana* is expressed in the xylem parenchyma cells of all roots and leaf vascular system by the AAP6-promoter (Okumoto et al., 2002). RNA-Blot Analysis shows that the AAP6 gene is strongly expressed in roots, shoot and stem leaves and weakly in the sprout and in the flower (Rentsch et al., 1996).

It is thus the task of the present invention to influence metabolism of a plant targetedly in the area of the xylem parenchyma of roots.

In accordance with the invention the set task is solved by a promoter which exhibits a tissue specific activity and is more active in xylem parenchyma cells of plant roots than in other cells of the plant.

Certain terms used in this application are described in greater detail in the following:

A promoter means a nucleic acid sequence, which controls the expression of a gene, in certain cases depending upon endogenous and exogenous factors. These factors include for example inductors, repressors and similar DNA-bonding proteins, however also environmental influences. A promoter can be comprised of multiple elements. It includes however at least one regulator element, which is responsible for the transcription of a gene under its control.

A promoter which is more active in parenchyma cells of plant roots than in other cells of the plant exhibits, for example in roots, an activity measurable by RNA-Blot, which is detectable in comparable experimental conditions in above-ground organs of the plant such as petioles, leaves and flowers at less than 20%, preferably at less than 10% and in particular at less than 5%. The specificity is not limited to a particular experimental time, but rather is fundamentally exhibited during the entire vegetative time.

"Derivatives" of a promoter are shortened or elongated or segments of identical versions or homologs of this promoter with the same or substantially the same characteristics.

"Pathogen inducability" means the influence of external factors on the plant, which are followed by a defensive reaction. These could be attacks by insects (grubs), bacteria, fungus, nematodes or other pathogens, however also abiotic influences, such as mechanical wounding or water or salt stress.

"Direct antifungal activity" means that gene products act directly antifungally, in that they, for example, dissolve cell walls or code for phytoalexinsynthases or, as the case may be, for metabolites which actively limit fungal metabolism.

"Indirect antifungal effect" means that gene products activate the plant genetic defenses. These include for example resistance genes, components of signal transduction (such as kinases, phosphatases), transcription factors or enzymes which produce signal substances (such as ethylene forming, salicylicic acid forming or jasmonate forming enzymes, reactive oxygen species forming enzymes, nitratemonoxide forming enzymes).

The term "infection" refers to the earliest point in time at which the metabolism of the fungus (for example the growth of the fungus) is prepared for penetration of the host tissue. This includes for example the outgrowth of hyphae or the formation of specific infection structures such as penetration hyphae and appressoria.

The expression "homology" as used herein means a homology of at least 70% at the DNA-level, which can be determined by known processes, for example computer controlled sequence comparison (S. F. Altschul et al., (1990), Basic Local Alignment Search Tool, J. Mol. Biol. 215: 403-410).

"Complimentary nucleotide sequence" means, with reference to a double stranded DNA, that the second DNA strand exhibits the nucleotide bases complimentary—according to the base pairing rules—to the first DNA strand, which correspond to the bases of the first strand.

The term "hybridized" used herein means hybridizing under conventional conditions, as described in Sambrook et al. (1989), preferably under stringent conditions. Stringent hybridization conditions are for example: hybridizing in 4×SSC at 65° C. and subsequent multiple washing in 0.1× SSC at 65° C. for a total of approximately one hour. Less stringent hybridization conditions are for example: hybridizing in 4×SSC at 37° C. and subsequent multiple washing in 1×SSC at room temperature. "Stringent hybridization conditions" can also mean: hybridizing at 68° C. in 0.25 M sodiumphosphate, pH 7.2, 7% SDS, 1 mM EDTA and 1% BSA for 16 hours and subsequent two times washing with 2×SSC and 0.1% SDS at 68° C.

The invention is described in greater detail in the following with reference to the figures and examples.

The inventive promoter is active in xylem parenchyma cells of plant roots. No activity or only a small amount of activity is detectable in the above ground organs of the concerned plant. This characteristic can be used for improving the charge and discharge processes of the xylem of the root and therewith can be used for improving the metabolism. By using the promoter it is thus also possible to provide transgenic plants and parts of these plants such as seeds.

The inventive promoter can be used to improve the nitrogen exchange of the plants. For this, transport protein genes for nitrate and amino acids are overexpressed in the root xylem parenchyma cells and the loading of the xylem is fortified with the N-compounds. A further improvement in the N-metabolism is provided by the reduced storage of "harmful nitrogens" in the storage organs of the plant. Elevated concentrations of nitrogen compounds in storage organs often reduce the nutrient physiological value of harvested products, or impede the isolation of stored compounds such as sucrose from sugar beet roots. The reduced storage of "harmful nitrogen" in the root can also be achieved by an amplified deposit of amino acids in the xylem and transporting in the aboveground plant organs.

The inventive promoter can be used to improve water stress tolerance of the plants. The concentration of the phytohormone abscisic acid (ABA) increases in the roots in reaction to the drying of the soil. ABA is transported from the roots via xylem into the leaves, where it causes a closing of the stomata. By a controlling the expression of the ABA-transporter in the xylem parenchyma cells the ABA entry into xylem can be regulated and the drought stress tolerance of the plants can be improved.

The inventive promoter can be used to reduce the concentration of the cations sodium (Na+) and potassium (K+) in the roots of sugar beets. The Na+/K+ concentration determines the processing quality of sugar beets with respect to the technical extraction of sugar (Schlweck et al., 1984). The Na+ and K+ transport molecules in the xylem parenchyma cells of the root have a key job for a low Na+/K+ concentration in the sugar beet root. With the aid of the promoter suitable processes can be carried out, in order to keep the Na+/K+ concentration low, for example the overexpression of the Na+/H+ Antiporter SOS1 (Shi et al., 2002) in the xylem parenchyma cells. On the other hand, the loading of the xylem K+ is regulated separately from the K+ uptake from the soil. While AKT1 is responsible for the K+ uptake from the medium, the K+ loading of the xylem occurs via the transport molecule SKOR (stelar K+ outward rectifier). The targeted overexpression of SKOR (Gaymard et al. 1998) would lead to an amplified transport of K+ out of the roots.

The inventive promoter can also be used to improve the disease resistance of plants. Numerous soil inhabiting fungus of this species *Fusarium oxysporum* or *Verticillium* spp. use the xylem for spreading in the plant. By combination of the pathogen inducible promoter with a gene, of which the gene product has a direct or indirect antifungal effect, the further spreading of the fungus in xylem can be prevented, and accordingly be fungus resistance can be realized. Herein the pathogen inducibility of the promoter takes on a particular role, in order to achieve in the xylem parenchyma a level of expression critical for the effectiveness of the antifungal working principle.

Viral infections of the sugar beet are often limited to one organ such as the root or the above-ground plant parts. Thus the virus BMYVV infects and colonizes predominantly the sugar beet root, and the yellowing virus BMYV and BYV are only found in the leaves. The root specific promoter can thus be used to organ-specifically translate or convert the virus resistance concepts involving gene silencing or as the case may be the antisense technique.

The file of this patent contains at least one drawing executed in color. Copies of this patent with color drawing(s) will be provided by the Patent and Trademark Office upon request and payment of the necessary fee.

FIG. 1 shows the root specific expression of the gene 2-1-88 by a RNA-Blot experiment. Respectively 10 μg whole cell-RNA, which were isolated from the organs of 2-year old flowering sugar beet, were separated in a denaturing formaldehyde agarosegel. RNA was isolated from the leaves, the plant root, the sprout and the flowers. The smart cDNA fragment 2-1-88 was used as hybridization testing probe.

FIG. 2 shows a reporter gene vector 2-1-88-GUS with a translational fusion between the Promoter (SEQ ID NO: 1) and the GUS-gene from *E. coli*. The promoter in the vector 2-1-88-GUS was isolated as HindIII-NcoI fragment and includes the nucleotide positions 1-2502 of the nucleotide sequence SEQ ID NO: 1.

FIG. 3 shows a reporter gene vector 2-1-88-LUC with a translational fusion between the promoter (SEQ ID NO: 1) and the luciferase gene from *Photinus pyralis*. The promoter 2-1-88 in the vector 2-1-88-LUC includes the nucleotide positions 1-2502 of the nucleotide sequence SEQ ID NO: 1.

Figure 7:
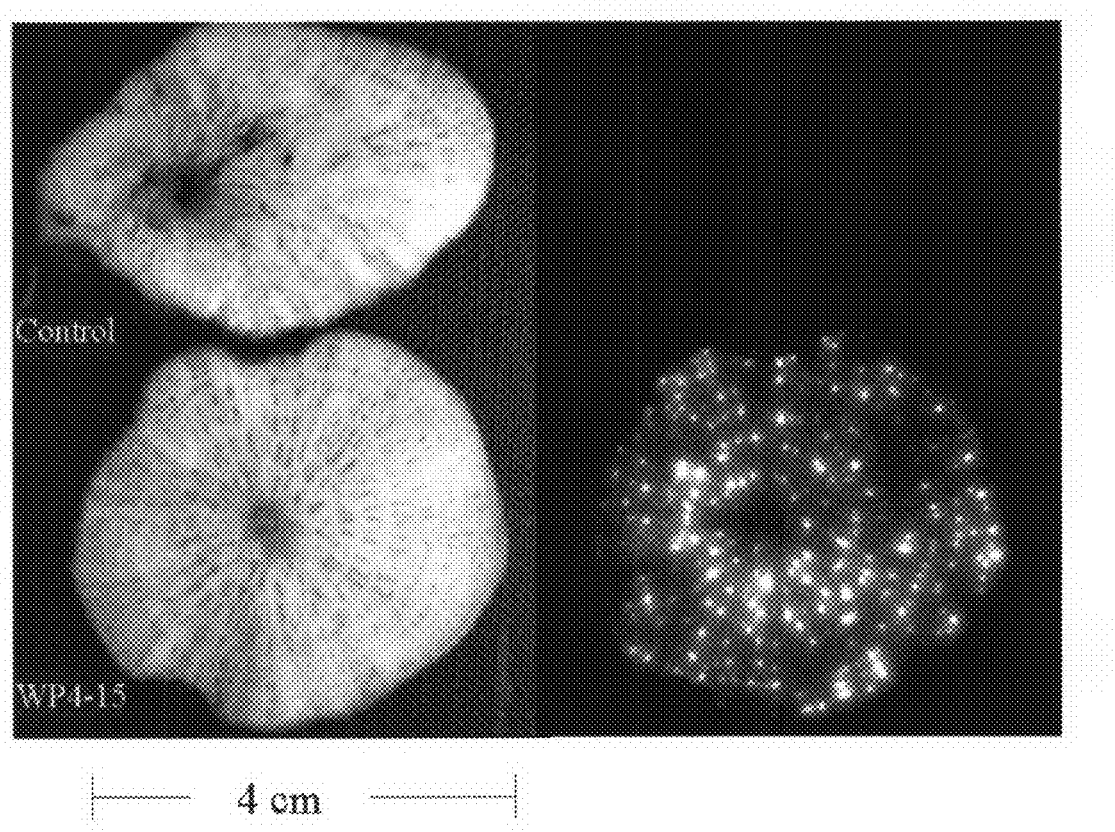

FIG. 7 shows a spatial distribution of the luciferase activity in the root cross section of the transgenic sugar beet line WP4-15 in comparison to nontransgenic starting line (control). The root discs were photographed under illumination (left) and then the light emission from the root disc in the dark was documented (right). The position and strength of the light emission correlated with the activity of the Promoter (SEQ ID NO: 1) in the root of the transformant WP4-15 (right bottom). The nontransgenic starting line shows no light emission (right upper).

Figure 8:
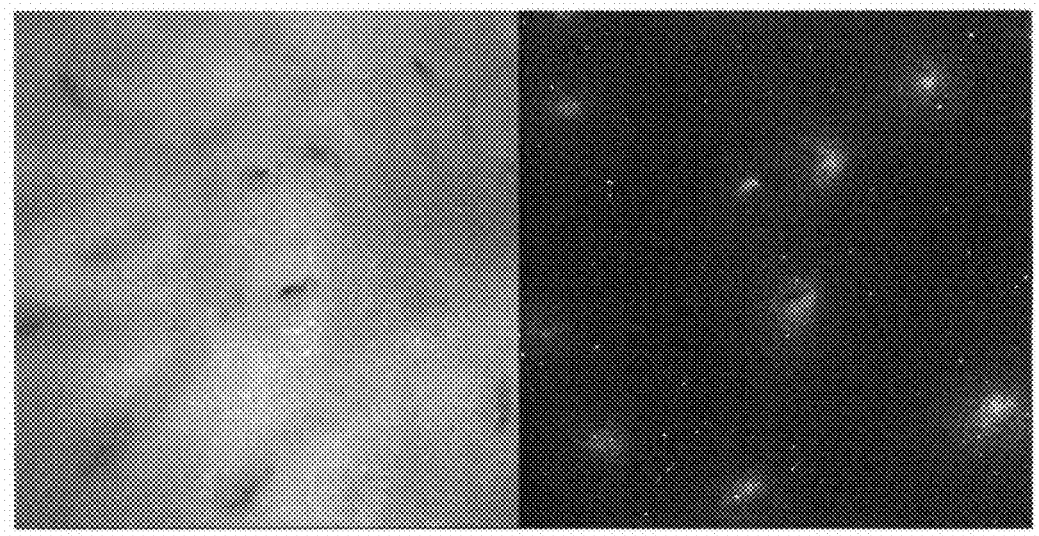

FIG. 8 shows a microscopic detail image of the transgenic root disc WP4-15 from FIG. 7. In the left image half the illuminated root surface can be seen. The vascular bundle comprised of phloem and xylem appears as dark slits. In the right image half the localization of the light emission about the xylem bundle is demonstrated. This image was recorded in the dark, so that only the light emission from the object was measured.

Figure 9:
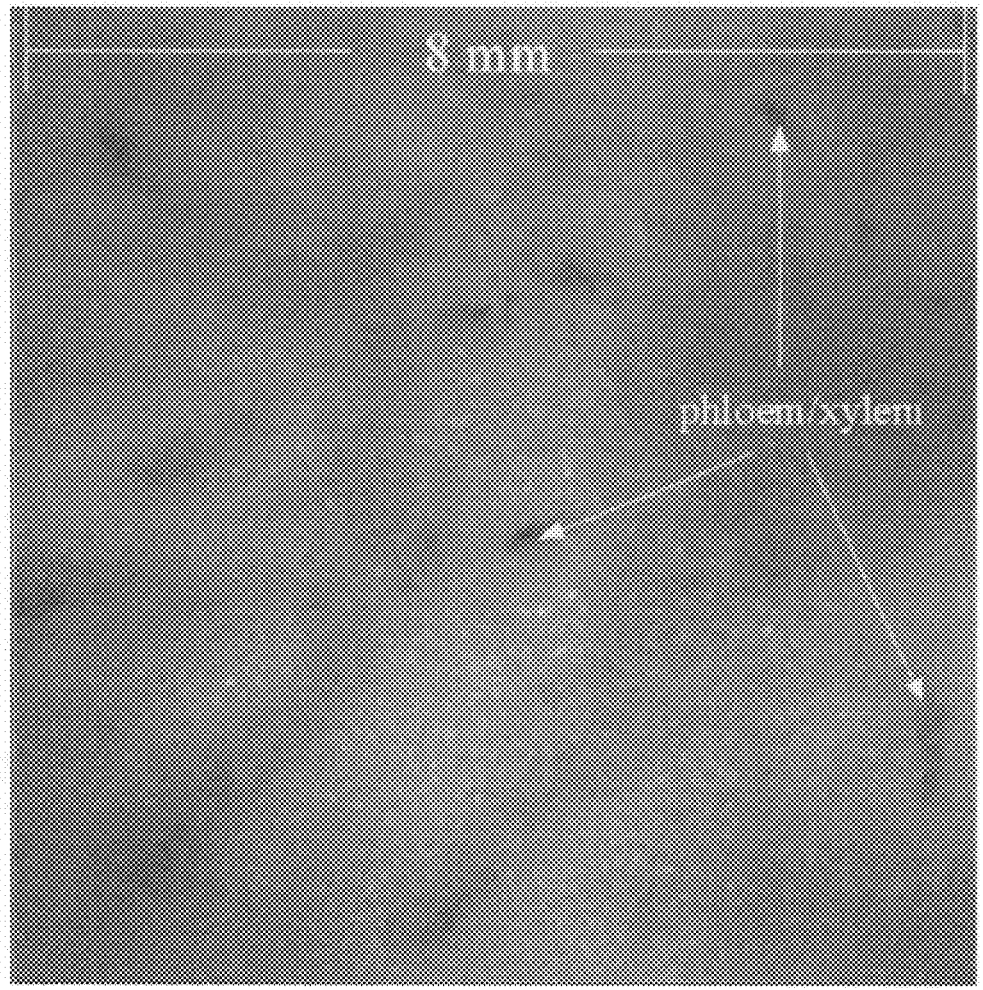

FIG. 9 shows a super-positioning of the left and the right image halves from FIG. 8. The luciferase reporter gene activity appears red in this figure. The reporter gene activity is limited to the cell layer between xylem and phloem or as the case may be the immediate vicinity about the xylem and the xylem parenchyma cells.

Figure 10:
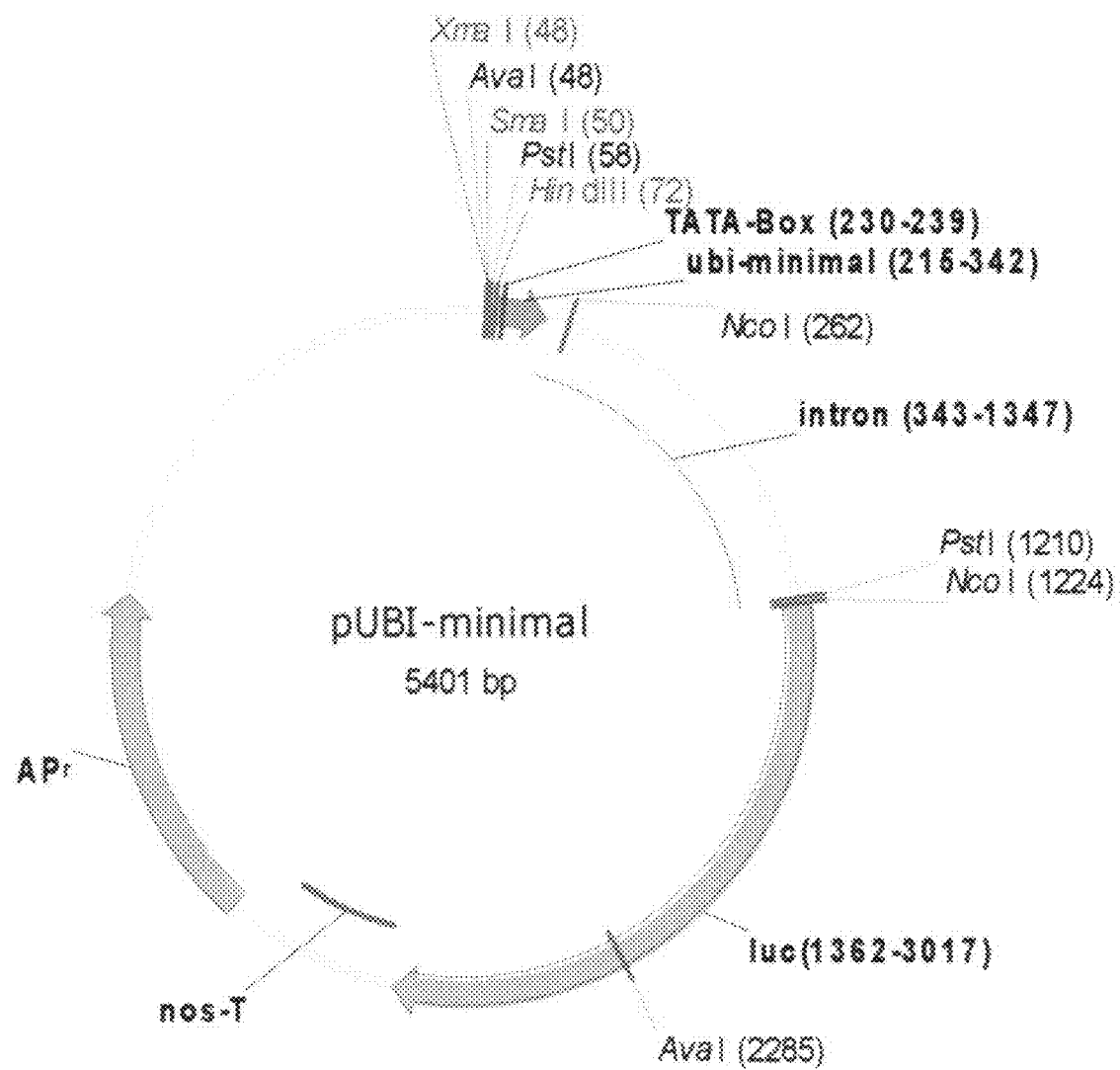

FIG. 10 shows a reporter gene vector pUB1-minimal with the minimal promoter of the ubiquitine promoter from corn.

CHARACTERIZING THE PROMOTER 2-1-88

Figure 4:
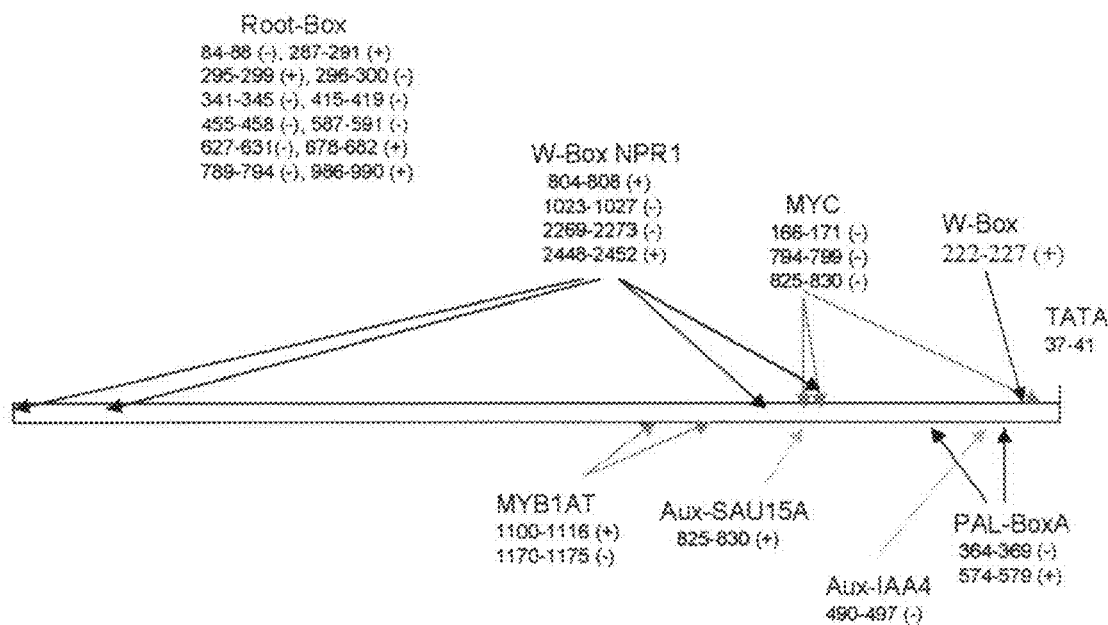
FIG. 4 shows a modular organization of the promoter (SEQ ID NO: 1) and the distribution of cis-elements.

The promotor (SEQ ID NO: 1) originated from a—previously unknown—sugar beet gene 2-1-88 and is in the following also referred to as 2-1-88 promoter. The analysis of this promoter with the aid of the PLACE data bank (Higo et al., 1999) shows that numerous cis-elements for pathogen induceability, root specificity as well as water and cold stress responsivity can be demonstrated (Table 1). One characteristic pathogen responsive element is W-Box, which occurs once as "classical" W-Box (Rushton et al., 2002) and four times as W-Box NPR1 (Yu et al., 2001) in the promoter (FIG. 4). Besides the core motif pattern TTGACC or as the case may be TTGAC, respectively the 15 nucleotides upstream and downstream of the W-core motif have important significance for the pathogen inducibility in combination with the core motif. Beyond this, the Box-A from the pathogen-inducible PcPAL promoter is present. The root specificity of the promoter is determined by the numerous root specific motives (root Box ATATT) and the cis-elements for auxinresponsivity (Aux-IAA4 and Aux-SAU15A) (Guilfoyle et al., 1998). The water, salt and cold stress inducibility of the promoter can be traced back to the presence of the MYC and MYB bonding sites (Abe et al., 2003), which are involved in the ABA signal transduction.

Fusion of the 2-1-88-Promoter with the Luciferice Gene of *Photinus Pyralis*

Figure 1:
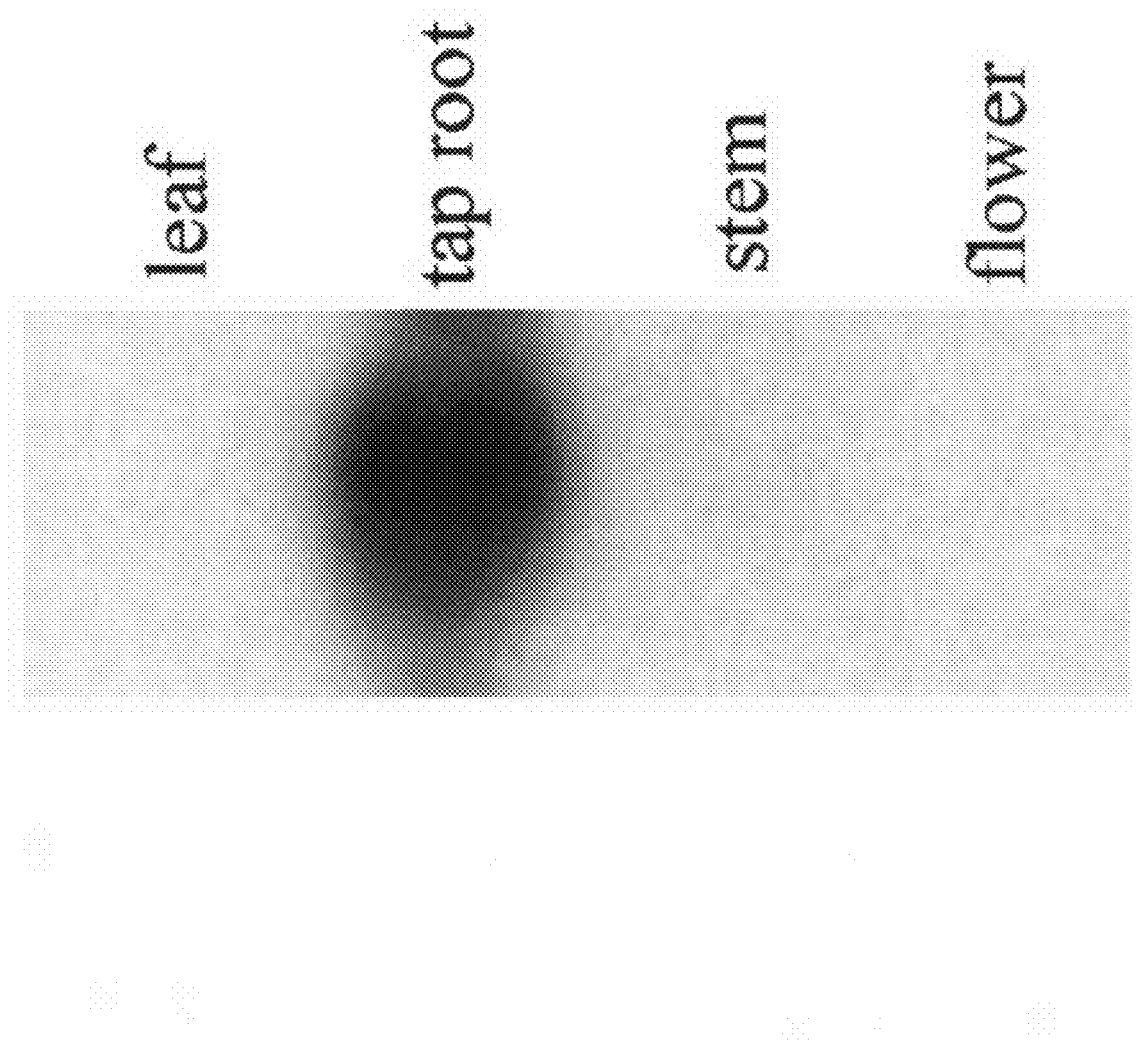
Figure 2:
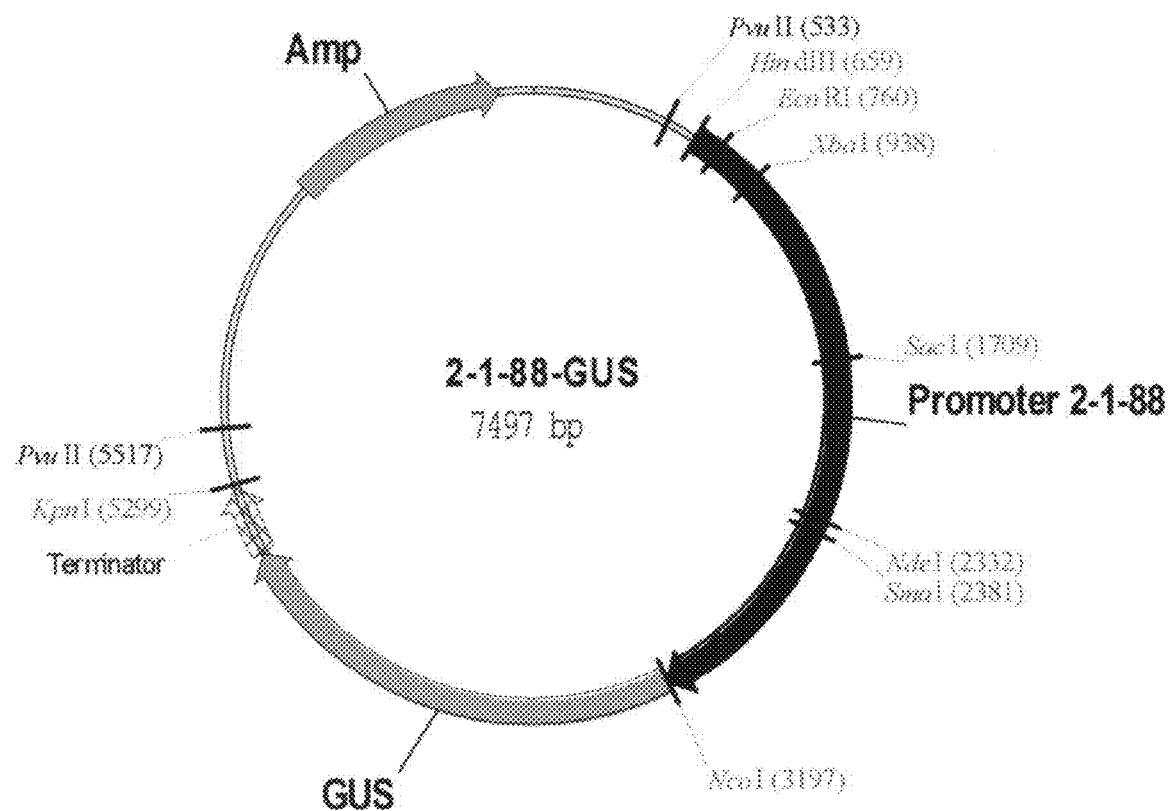
Figure 3:
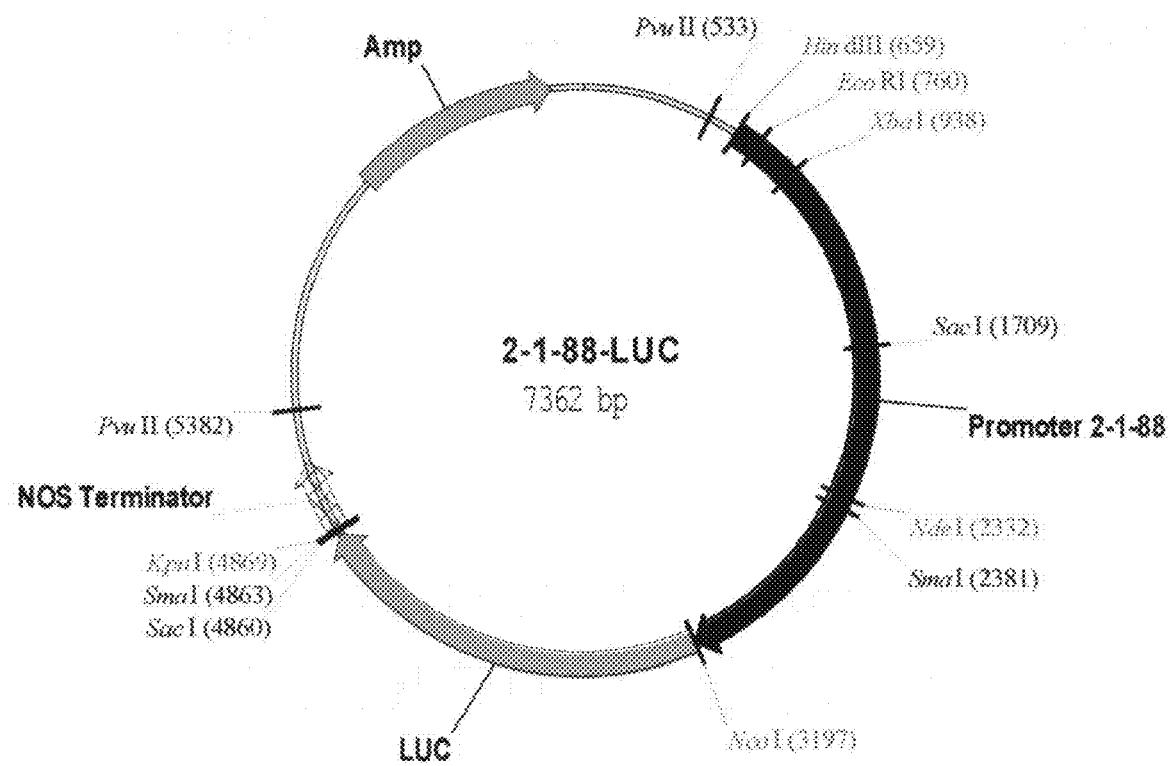

In order to demonstrate the activity of the 2-1-88 promoter in sugar beets, the promoter was translationally fused in the luciferase gene from *photinus pyralis* and transformed in sugar beets. For this the victor 2-1-88-GUS was first linearized by a SacI cleavage with subsequent T4-DNA-Polymerase-replenishing reaction. By subsequent digestion with NcoI the GUS-gene was released. In the thus-prepared vector the luciferase gene from *photinus pyralis* (Promega, Mannheim Germany) was cloned as NcoI-BgIII (replenished) fragment. The resulting vector carried the characteristic 2-1-88-LUC (FIG. 3) and contained a translational fusion between the 2-1-88 promoter and the luciferase gene.

Figure 5:
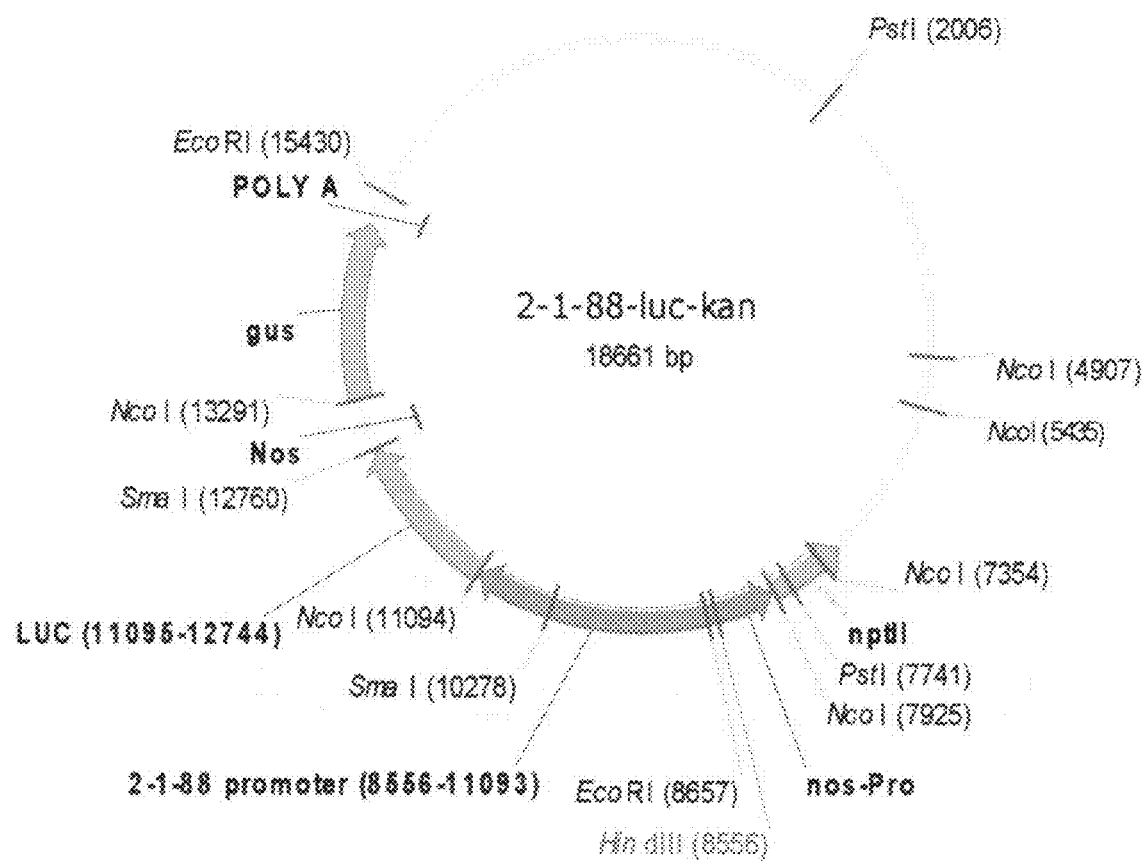
FIG. 5 shows a binary vector 2-1-88-luc-kan, which was used for sugar beet transformation.

For the transformation of the sugar beet the expression cassette comprised of the 2-1-88-promoter and the luciferase gene was cloned over in the binary vector pGPV-kan (Becker et al., 1992). For this the 2-1-88-promoter-luciferase gene-combination with PvuII and HindIII was cut out of the vector 2-1-88-LUC and cloned in the binary vector pGPTV-kan linearized with HindIII and SmaI. The resulting vector was given designation 2-1-88-luc-kan (FIG. 5). The vector 2-1-88-luc-kan was transformed in the agrobacterium tumefaciens line C58C1 with the resident plasmid pGV2260 by a direct DNA-transformation process (An, 1987). The selection of recombinant *A. tumefaciens* clones occurred by use of the antibiotic kanamycin (50 mg/l).

The transformation of the sugar beets occurred according to Lindsey et al. (1991) with use of the antibiotic kanamycin. The transgenesisity of the plants was verified by PCR. The use of the primary GTGGAGAGGCTATTCGGTA and CCACCATGATATTCGGCAAG lead to the amplification of a 553 bp DNA fragment from the nptII gene. The PCR was carried out using 10 ng genomic DNA, a primer concentration of 0.2 µM at an annealing temperature of 55° C. in a Multi-cycler PTC-200 (MJ Research, Watertown, USA).

Confirmation of the 2-1-88 Promoter Activity in Roots of Transgenic Sugar Beets

Transgenic sugar beets, which were transformed with the reporter gene contruct 2-1-88-luc-kan, were raised in greenhouse conditions. The activity of the promoter was analyzed in roots and leaves of young and old sugar beets by reporter gene measurements.

The *Photinus pyralis*-Luciferase activity was determined using a Luciferase Assay System (Promega, Mannheim, Germany) in a Sirius Luminometer (Berthold Detection System GmbH, Pforzheim, Germany) in accordance with the manufacturer's specifications. For extracting an enzyme extract suitable for the measurements, first the weight of the tissue sample was determined. The leaf samples were homogenized with addition of sea sand with a 10-fold volume (v/w) of Passive Lysis Buffer (PLB) in a mortar and the root sample was homogenized in a conventional kitchen apparatus (Warring Blender). The liquid supernatant was transferred into a 1.5 ml-Eppendorf vessel and centrifuged 5 min at 4° C. and 20,000 g. The clear supernatant was removed and respectively 10 µl raw extract were introduced for the *Photinus* luciferase activity measurement.

Figure 6:
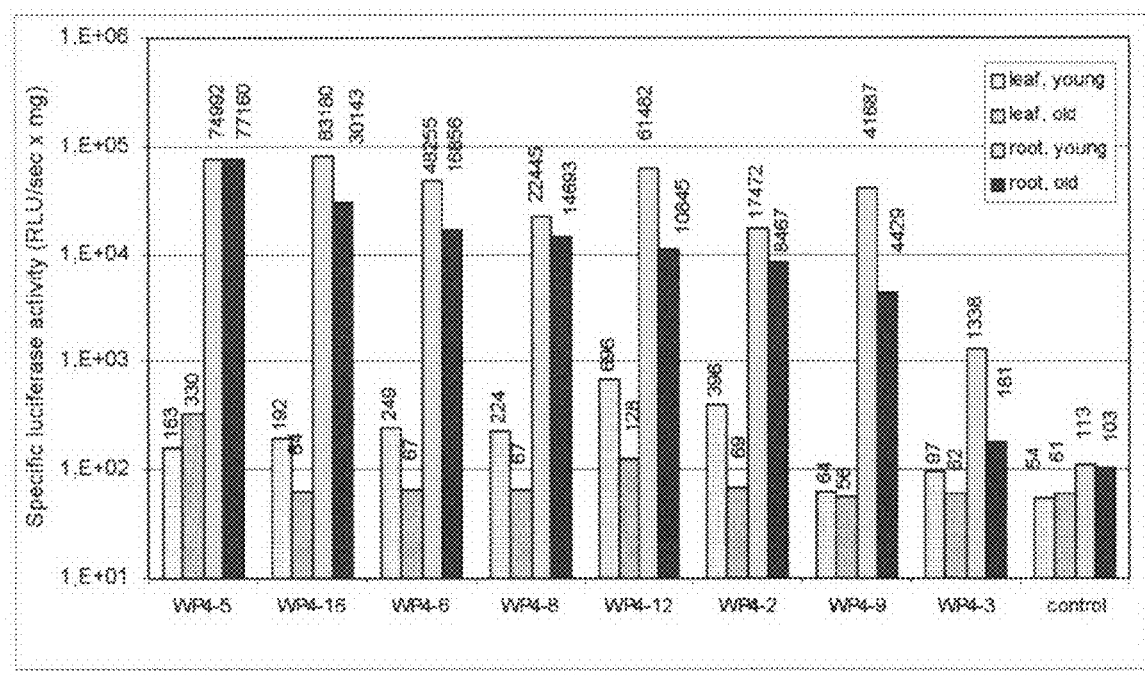
FIG. 6 shows a specific luciferase activity of the reporter gene construct 2-1-88-luc-kan in extract from roots and leaves of younger and older transgenic sugar beets (WP4) as well as the activity of the nontransgenic starting line (control). The scaling of Y-axis is logrithmic.

While the promoter (SEQ IDS NO: 1) was strongly, or as the case may be very strongly, expressed in the young and the old roots of 9 independent transformants, and the reporter gene activity in 7 transformants (WP4-2, WP4-5, WP4-6, WP4-8, WP4-9, WP4-12, WP4-16), in comparison to the nontransgenic starting line in which it was hardly demonstratible in young plants and not in old plants (FIG. 6). The promoter (SEQ ID NO: 1) was primarily expressed in the root of the sugar beet according to the results of the reporter gene study which correlated with the RNA-blot-study.

The 2-1-88 Promoter is Speficially Active in the Xylem Parenchyma Cells of the Sugar Beet Root In order to analyze the spatial distribution of the promoter activity in the sugar beet roots, transverse and longitudinal sections of the beet were prepared and the root sections incubated 2-4 hours in a solution of 100 µM luciferin plus 5% DMSO at room temperature. Subsequently the light emission from the root sections, which can be traced back to the luficerase activity, were detected with the aid of a MicroMAX Digital CCD Camera (Visitron Systems GmbH, Puchheim, Germany).

The analysis of the cross sections showed that the promoter activity is associated with the position of the vascular cells in the individual cambriun rings of the root (FIG. 7). For a detailed analysis the stereo-microscope Stemi 2000 (Zeiss, Germany) was equipped with a camera with the aid of HRD microscope adaptor. According to the microscopic analysis the promoter activity is limited to the xylem parenchyma cells between xylem and phloem or as the case may be the xylem parenchyma cells surrounding the xylem (FIGS. 8 and 9).

With the inventive promoter, transgenic plants with particular characteristics can be produced:

a. improved charging and discharging processes of the xylem in the root,
b. improved nitrogen uptake,
c. reduced accumulation of "harmful nitrogen" in the root,
d. improved salt resistance,
e. improved drought stress resistance,
f. improved frost tolerance,
g. improved Na+/K+ concentration in the root, and
h. elevated resistance/tolerance to pathogens.

The 2-1-88 Promoter is Induced in the Xylem Parenchyma Cells by Biotic and Abiotic Stress Transgenic WP4 sugar beets, which were transformed with the reporter gene construct 2-1-88-luc-kan, were infected with the parasitic fungus *Fusarium oxysporum f.* sp. betae. *Fusarium oxysporum f.* sp. betae is a vascular pathogen of beet, which propagates in the xylem system of the plant and causes fusarium deadhead. Four weeks after infection, the luciferase reporter gene activity in the infected root was quantified. The reporter gene activity was significantly increased in the infected roots in comparison to the noninfected transgenic plants. The 2-1-88-promoter was less induced by pathogen infestation. The analysis of the special distribution of the reporter gene activity with the aid of the CCD-camera showed that the promoter activity was significantly higher in the xylem parenchyma cells which surrounded the infected xylem bundle.

Change of the Nitrogen Metabolism of Plants

The nitrogen metabolism of plants can be improved in many respects by the use of the inventive promoter. The specific elevation or reduction of the number of suitable transport proteins in the xylem parenchyma cells of the root improved the uptake and the transport of N-compounds in the plant.

By the root-specific expression of transport protein genes for nitrate ions in xylem parenchyma, the nitrogen uptake from the soil can be increased and the utillization of N-fertilizers can be improved. The improved nitrate transport in the above-ground plant parts leads to an elevated amino acid production in the leaves. A more efficient utilization of the N-compounds already reduced to amino acids in the roots serves, or is served by, the xylem parenchyma specific expression of amino acid transporters by the promoter.

A further improvement of the N-metabolism results from the reduced storage of "harmful nitrogen" in the storage organs of the plant. Elevated concentrations of N-compounds in the storage organs often reduce the nutrient physiological value of harvested products or complicate the extraction of stored substances such as sucrose from sugar beet roots. A reduced storage of "harmful nitrogen" in the sugar beet root can be accomplished by the amplified transport of amino acids out of the root into the above ground plant parts via the xylem. For this, appropriate amino acid transporters are overexpressed.

Increasing the Tolerance to Phytopathogenic Viruses

Numerous phytopathogenic virus of sugar beet have an organ specificity, that is, the viral replication occurs generally not in the entire plant, but rather only in a particular organ or tissue-type. Likewise the damage, brought about by the viral infection, as a rule is limited to the afflicted organ. Viral disease inducers of sugar beet with organ specificity include for example BNYVV with the preference for roots and BNYV and BYV with the limitation to beet leaves.

The inventive promoter can be used to develop a root specific BNYVV resistance in sugar beet. For this, for the transformation of the gene-silencing-dependent virus resistance strategy, a native or mutated DNA partial sequence of the viral BNYVV-genome was combined with the promoter. The combination of the promoter sequence and the viral DNA sequence was so designed, that the transcription of the BNYVV sequence lead to a gene silencing effective against the BNYVV. The effectiveness of the adoption of the approach was determined via a determination of the virus titer in the plants with utilization of an ELISA-test, which is directed against the coat protein of BNYVV.

Increased Tolerance of Transgenic Plants Against Soil Propagating Phytopathogenic Fungi The inventive promoter can also be used, in combination with a gene or a gene combination, to impart a direct or indirect antifungal effect in the roots of plants. The antifungal effect leads to an elevated fungal resistance or fungal tolerance particularly against vascular parasites such as *Fusarium oxysporum* spp.

For this the promoter is fused with genes of the pathogen defense, of which the gene product have a direct or indirect antifungal effect, translationally or transcriptionally. The promoter gene combinations are cloned in a binary transformation vector pGPTV and transformed by *A. tumefaciens* mediated transformation in sugar beet, potato or rape. The transgenicity of the plants was verified by PCR as already described and the expression of the gene and the roots was verified by RNA-blot studies. The elevated fungal resistance of the plants was observed in fungal resistance tests.

Suprisingly, the root- and xylem parenchyma-specific induced expression of pathogen defense did not lead to dwarfism or reduced tolerance often observed in the case of constitutive expression in the total plant (Heil and Baldwin, 2002). A further advantage of the essentially root specific gene expression is that the resistance imparting gene product is formed only in the organ to be protected. Commercially important plant parts such as rape seed thus remain free of any transgenic products.

Genes, of which the products have an indirect, antifungal effect, require a particularly careful expression control, in order to avoid negative consequences of an undesired activation of the plant defense mechanism. One example for an indirect, antifungal effect is the effect which stems from the coexpression of the plant resistance-R-gene in combination with an avirulence-(avr)-gene or the overexpression of an auto-activated R-gene in a plant cell. The join expression of R and avr-genes or the singular expression of an auto-activated R-gene leads to an intensive activation of the plant defense mechanism and requires a strict regulation. The regulation is achieved, in that either the R-gene or the avr-gene is placed under the control of the inventive promoter.

Use of the Inventive Promoter in Monocotyledons

Although the promoter is also active in monocotyledons, an optimal activity of the promoter in monocotyledons is achieved when a sugar beet minimal promoter inclusive TATA-Box is replaced by a minimal promoter of the ubiquitin promoter from corn inclusive the intron (SEQ ID NO: 2). For this, the SEQ ID NO: 1 from Position 1-2459 is amplified by PCR and cloned with the vector pUBI-minimal cleaved with SmaI (FIG. 10).

This disclosure incorporates by reference the entirety of the electronically-submitted text file entitled "Sequence_listing" having a size of 6 kb, created Mar. 26, 2007.

REFERENCES

Abe, H., Urao, T., Ito T. Seki, M., Shinozaki, K., and Yamaguchi-Shinozaki K. (2003). Arabidopsis AtMYC2 (bHLH) and AtMYB2 (MYB) function as transcriptional activators in abscisic acid signaling. Plant Cell. 15(1) :63-78.

Altschul, S. F. et al. (1990). Basic Local Alignment Search Tool, J. Mol. Biol. 215: 403-410

An, G. (1987). Binary Ti vectors for plant transformation and promoter analysis. Methods Enzymol.153, 292-305.

Becker D, Kemper E, Schell J. and Masterson R. (1992). New plant binary vectors with selectable markers located proximal to the left T-DNA border. Plant Mol Biol. 20(6): 1195 7.

Elmayan, T. and Tepfer M. (1995). Evaluation in tobacco of the organ specificity and strength of the roID promoter, domain A of the 35S promoter and the 35S2 promoter. Transgenic Res. 4(6):388-96.

Gaymard F., Pilot G., Lacombe B., Bouchez D, Bruneau D, Boucherez J., Michaux-Ferriere N., Thibaud J B, Sentenac H. (1998). Identification and disruption of a plant shaker-like outward channel involved in K+ release into the xylem sap. Cell 94, 647-655.

Guilfoyle, T., Hagen, G., Ulmasov, T., and Murfett, J. (1998). How does auxin turn on genes? Plant Physiol.118(2):341-7.

Heil, M. and Baldwin, I. T. (2002). Fitness costs of induced resistance: emerging experimental support for a slippery concept. Trends Plant Sci. 2002 February; 7(2):61-7.

Higo, K., Ugawa, Y., Iwamoto, M. and Korenaga, T. (1999). Plant cis acting regulatory DNA elements (PLACE) database:1999. Nucleic Acid Research 27: 297-300.

Lindsey, K., Gallois, P., and Eady, C. (1991) Regeneration and transformation of sugar beet by Agrobacterium tumefaciens. Plant Tissue Culture Manual B7: 1-13; Kluwer Academic Publishers.

Logemann, E., Parniske. M., Hahlbrock, K. (1995). Modes of expression and common structural features of the complete phenylalanine ammonia-lyase gene family in parsley. Proc Natl Aced Sci U S A. 1995 92(13):5905-9.

Mes J J, van Doom A A, Wijbrandi J. Simons G., Cornelissen B J, and Haring M A. (2000). Expression of the Fusarium resistance gene 1-2 colocalizes with the site of fungal containment. Plant J. 23(2): 183-93.

Okumoto S., Schmidt R., Tegeder M, Fischer W N, Rentsch D, Frommer W B, and Koch W. (2002). High affinity amino acid transporters specifically expressed in xylem parenchyma and developing seeds of Arabidopsis. J Biol Chem. 277(47):45338-46.

Rentsch D., Hirner, B., Schmelzer, E., and Frommer W. B. (1996). Salt stress-induced proline transporters and salt stress-repressed broad specificity amino acid permeases identified by suppression of a yeast amino acid permease-targeting mutant. Plant Cell. 1996. August; 8(8):1437-46.

Rushton, P. J., Reinstadler. A., Lipka. V, Lippok, B., and Somssich, I, E. (2002). Synthetic plant promoters containing defined regulatory elements provide novel insights into pathogen- and wound-induced signaling. Plant Cell.14(4): 749-62.

Sambrook, J., Fritsch, E. F., and Maniatis, T (1989). In Molecular Cloning, A Laboratory Manual (Cold Spring Harbor Laboratory Press, New York).

Schiweck, H., Kozianowski, G., Anderlei, J. and Burba, M. (1984). Errechnung der Dicksaft-Nichtzuckermasse aus Rübenanalysen. Zuckerindustrie 119, 268-282.

Shi H. Quintero F J, Pardo J M, Zhu J K. (2002). The putative plasma membrane Na(+)/H(+) antiporter SOS1 controls long-distance Na(+) transport in plants. Plant Cell 14, 465-477.

Takahashi H. Watanabe-Takahashi A, Smith F W, Blake-Kalff M, Hawkesford M J, and Saito K. (2000). The roles of three functional sulphate transporters involved in uptake and translocation of sulphate in Arabidopsis thaliana. Plant J.23(2):171-82.

Yu, D., Chen, C., and Chen, Z. (2001). Evidence for an important role of WRKY DNA binding proteins in the regulation of NPR1 gene expression. Plant Cell. 2001 (7): 1527-40.

TABLE 1

Organization of the cis-Elements in the Promoter 2-1-88

| Cis-Element (Sequence) | Position[1] | Function |
|---|---|---|
| TATA Box (TATAAA) | 36-41 (+) | Binding site of the basal transcriptionfactor complex |
| Root-Box (ATATT) | 84-88 (−), 287-291 (+) 295-299 (+), 296-300 (−) 341-345 (−), 415-419 (−) 455.458 (−), 587-591 (−) 627-631 (−), 678-682 (+) 789-794 (−), 986-990 (+) | Element for root specificity from the rol D promoter (Elmayan and Tepfer, 1995). |
| MYC Consensus (CANNTG, N = A, T, C, G) | 166-171 (−) 794-799 (−) 825-830 (−) | MYB Core-bonding site from the drought stress responsive promoter rd22 and other genes (CBF3), involved in the ABA- and cold signal transduction (Abe et al., 2003) |
| W-Box (TTGACC) | 222-227 (+) | Core-motif of WRKY bonding site of PcPR1-1 and PcPR1-2, sufficient for the pathogen induction of synthetic promotors (Rhushton et al., 2002) |
| PAL-BoxA (CCGTCC) | 364-369 (−) 574-579 (+) | Box A from the pathogen responsive PcPAL promoter (Logemann et al., 1998) |
| Aux-IAA4 (G/TGTCCCAT) | 490-497 (−) | Auxin responsive cis-element from PS IAA4/5 promoter per Gullfoyle et al. (1998) |
| W-Box NPR1 (TTGAC) | 804-808 (+) 1023-1027 (−) 2269-2273 (−) 2448-2452 (+) | Core-motive of the WRKY bonding site of AtNPR1, responsible for pathogen induction (Yu et al., 2001) |
| Aux-SAU15A (CATATG) | 825-830 (+) | Auxin responsive cis-Element from SAUR15A Promoter per Guilfoyle et al. (1998) |
| MYB1AT (A/TAACCA) | 1100-1116 (+) 1170-1175 (−) | MYB bonding site from the drought stress responsive promoter rd22, involved in the ABA-signal transduction (Abe et al., 2003). |

The indicated positions are with reference to the transcription starting point (+1).
(+) = direct Orientaton to the TATA-Box,
(−) = reverse Orientation to the TATA Box.

The invention claimed is:

1. A promoter, comprising a nucleotide sequence selected from the group consisting of:
   (a) SEQ ID NO: 1;
   (b) a nucleotide sequence complementary to the full length of the nucleotide sequence according to SEQ ID NO: 1;
   (c) a nucleotide sequence having transcriptional promoter activity, which hybridizes under stringent hybridizing conditions with the nucleotide sequence according to SEQ ID NO: 1; and
   (d) a nucleotide sequence which hybridizes under stringent hybridizing conditions with the nucleotide sequence complementary to the nucleotide sequence according to SEQ ID NO: 1, wherein said sequence that hybridizes has transcriptional promoter activity, and wherein the stringent hybridizing conditions are either:
      (1) hybridizing in 4×SSC at 65° C. and subsequent multiple washing in 0.1×SSC at 65° C. for a total of approximately 1 hour; or
      (2) hybridizing at 68° C. in 0.25 M sodium phosphate, pH 7.2, 7% SDS, 1 mM EDTA and 1% BSA for 16 hours and subsequent washing twice with 2×SSC and 0.1% SDS at 68° C.

2. A vector or mobile genetic element, containing the promoter according to claim 1 or a derivative thereof.

3. Monocot or dicot root cells, containing the promoter according to claim 1 or a derivative thereof.

4. A transgenic plant or part thereof, containing the promoter according to claim 2 or a derivative thereof.

5. Transgenic plant according to claim 4, wherein the plant is *Beta vulgaris*.

6. A plant part according to claim 4, wherein said plant part is a seed.

7. A method for producing a transgenic plant with one or more of the following characteristics:
   a. improved loading/charging and unloading/discharging processes of the xylem in the root,
   b. improved nitrogen supply,
   c. reduced accumulation of "detrimental nitrogen" in the root,
   d. improved salt resistance,
   e. improved drought resistance,
   f. improved frost tolerance,
   g. modified Na+/K+ concentration in the root,
   h. elevated resistance/tolerance to pathogens, said method comprising transforming a plant with a promoter according to claim 2.

* * * * *